United States Patent
Wang et al.

(10) Patent No.: US 10,709,652 B2
(45) Date of Patent: Jul. 14, 2020

(54) SKIN CARE COMPOSITION

(71) Applicant: Conopco, Inc., Englewood Cliffs, NJ (US)

(72) Inventors: Bingqing Wang, Shanghai (CN); Zheng Wang, Shanghai (CN); Qian Zhang, Shanghai (CN); Xia Zheng, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/309,662

(22) PCT Filed: May 16, 2017

(86) PCT No.: PCT/EP2017/061660
§ 371 (c)(1),
(2) Date: Dec. 13, 2018

(87) PCT Pub. No.: WO2017/220254
PCT Pub. Date: Dec. 28, 2017

(65) Prior Publication Data
US 2019/0247292 A1 Aug. 15, 2019

(30) Foreign Application Priority Data
Jul. 25, 2016 (EP) .................................... 16181021

(51) Int. Cl.
*A61K 8/49* (2006.01)
*A61K 8/29* (2006.01)
*A61K 8/73* (2006.01)
*A61Q 17/04* (2006.01)
*A61K 8/06* (2006.01)

(52) U.S. Cl.
CPC .............. *A61K 8/496* (2013.01); *A61K 8/062* (2013.01); *A61K 8/29* (2013.01); *A61K 8/732* (2013.01); *A61Q 17/04* (2013.01)

(58) Field of Classification Search
None
See application file for complete search history.

(56) References Cited

U.S. PATENT DOCUMENTS

| | | |
|---|---|---|
| 2005/0008605 A1 | 1/2005 | L'Alloret |
| 2005/0207999 A1 | 9/2005 | Vernaire et al. |
| 2006/0177394 A1 | 8/2006 | Candau |
| 2006/0280714 A1 | 12/2006 | Maningat et al. |
| 2007/0020216 A1 | 1/2007 | Reinhart et al. |
| 2008/0044365 A1 | 2/2008 | Simonnet et al. |
| 2009/0068255 A1 | 3/2009 | Yu et al. |
| 2011/0020250 A1 | 1/2011 | Breyfogle et al. |
| 2011/0033400 A1 | 2/2011 | Ehlis et al. |
| 2012/0128601 A1 | 5/2012 | Behler |
| 2016/0015614 A1 | 1/2016 | Mann et al. |

FOREIGN PATENT DOCUMENTS

| | | |
|---|---|---|
| GB | 2439618 | 1/2008 |
| WO | WO2013049599 | 4/2013 |

OTHER PUBLICATIONS

Search Report and Written Opinion in EP16181021; dated Feb. 10, 2017.
IPRP2 in PCTEP2017061660; May 24, 2018.
Search Report and Written Opinion in PCTEP2017061660; dated Jun. 28, 2017.

*Primary Examiner* — Nannette Holloman
(74) *Attorney, Agent, or Firm* — Edward A. Squillante, Jr.

(57) ABSTRACT

Disclosed is a skin care composition comprising starch, benzotriazole derivative sunscreen, whitening pigment and a cosmetically acceptable carrier, wherein the starch is present in amount of less than 2.2% by weight of the composition, and the benzotriazole derivative sunscreen is present in amount of less than 0.22% by weight of the composition.

16 Claims, No Drawings

SKIN CARE COMPOSITION

FIELD OF THE INVENTION

The present invention relates to a skin care composition, In particular, the skin care composition is capable of providing excellent spreading sensory (creaminess) to consumers.

BACKGROUND OF THE INVENTION

Skin care compositions of various kinds are widely used by consumers. Skin care compositions such as moisturizing lotions or creams are applied to obtain benefits of anti-aging, skin lightening and moisturizing, while make-up skin care compositions are applied to obtain desired optics and color benefits.

Besides benefits delivered by the skin care compositions, sensory is also one of the most important factors that appeal to consumers, in particular the sensory when consumers apply the products, for example product creaminess. However, some skin compositions would leave the consumer with poor sensory sensations due to the existence of some ingredients in the composition.

Therefore, we have recognized that there is an increasing need to develop skin care compositions with desirable sensory sensations upon application. This invention, therefore, is directed to a skin care composition comprising starch, benzotriazole derivative sunscreen, whitening pigment and a cosmetically acceptable carrier, wherein the starch is present in amount of less than 2.2% by weight of the composition, and the benzotriazole derivative sunscreen is present in amount of less than 0.22% by weight of the composition which unexpectedly result in superior creaminess perception to consumer upon application.

SUMMARY OF THE INVENTION

In a first aspect, the present invention provides a skin care composition comprising starch, benzotriazole derivative sunscreen, whitening pigment and a cosmetically acceptable carrier, wherein the starch is present in amount of less than 2.2% by weight of the composition, and the benzotriazole derivative sunscreen is present in amount of less than 0.22% by weight of the composition.

All other aspects of the present invention will more readily become apparent upon considering the detailed description and examples which follow.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Particle diameter" as used herein refers to particle diameter in non-aggregated state unless otherwise stated. For polydisperse samples having particulate with diameter no greater than 1 µm, average particle diameter means the z-average diameter measured, for example, using dynamic light scattering (see international standard ISO 13321) with an instrument such as a Zetasizer Nano™ (Malvern Instruments Ltd, UK) unless otherwise stated. For polydisperse samples having particulate with diameter no less than 1 µm, diameter means the apparent volume median diameter (D50, also known as ×50 or sometimes d(0.5)) of the particles measurable for example, by laser diffraction using a system (such as a Mastersizer™ 2000 available from Malvern Instruments Ltd) meeting the requirements set out in ISO 13320 unless otherwise stated.

"Creaminess" for the purpose of this invention refers to the smooth texture and fine feel when spreading the skin care products on the skin, a desirable rheological characteristic for skin care product, determined by an expert sensory panel.

The term "starch" or "starches" for purposes of this invention mean not only native but also physically and chemically modified starches. Typical starches may be selected from tapioca, corn, barley, spelt, potato, sweet potato, banana, wheat, rice, sago, amaranth, sorghum, waxy maize, waxy tapioca, waxy potato, and high amylase starches containing greater than 40% amylase. Physically modified starches include gelatinized starches, fully or partially hydrated starches and destructurized starches as well as crosslinked starches. Chemically modified starch are those that have undergone acylation, alkylation, epoxidization, quaternization, carboxylation, phosphorylation, etherification (e.g. reaction with propylene or ethylene oxide), or esterification (e.g. reaction with acetic anhydride). Preferably the starch is chemically modified starch, in particular starches that have undergone esterification. More preferred chemically modified starch are starch octenyl succinate, hydroxypropyl starch phosphate or a mixture thereof, even more preferred chemically modified starch are aluminum starch octenyl succinate, sodium hydroxypropyl starch phosphate or a mixture thereof. The most preferred starch is aluminum starch octenylsuccinate. Such aluminum starch octenylsuccinate is commercially available from suppliers like Akzo Nobel under the names Dry flo pure.

The starch is preferably present in amount of from 0.001 to 2%, more preferably from 0.01 to 1.9%, even more preferably from 0.1 to 1.7%, still even more preferably from 0.4 to 1.4% and most preferably from 0.6 to 1.2% by weight of the composition.

Preferably, the benzotriazole derivative sunscreen is benzotriazolyl dodecyl p-cresol, sodium benzotriazolyl butylphenol sulfonate, methylene bis-benzotriazolyl tetramethylbutylphenol, or a mixture thereof. More preferably the benzotriazole derivative sunscreen is methylene bis-benzotriazolyl tetramethylbutylphenol. The methylene bis-benzotriazolyl tetramethylbutylphenol is commercially available from suppliers like BASF under the names Tinosorb M.

The benzotriazole derivative sunscreen is preferably present in amount of from 0.001 to 0.2%, more preferably from 0.01 to 0.18%, even more preferably from 0.05 to 0.15%, and still even more preferably from 0.07 to 0.12% by weight of the composition.

To have a better product sensory, for example thickness, wetness, creaminess, and/or stickiness, the weight ratio of the starch to the benzotriazole derivative sunscreen is preferably from 1:1 to 20:1, more preferably 5:1 to 10:1.

Whitening pigments are typical particles having a refractive index of greater than 1.3, preferably greater than 1.8 and most preferably from 2.0 to 2.7. Examples of such whitening pigment are those comprising bismuth oxy-chloride, boron nitride, barium sulfate, mica, silica, titanium dioxide, zirconium oxide, aluminium oxide, zinc oxide or combinations thereof. More preferred whitening pigment are particles comprising titanium dioxide, zinc oxide, zirconium oxide, mica, iron oxide or a combination thereof. Even more preferred whitening pigment are particles comprising zinc oxide, zirconium oxide, titanium dioxide or a combination thereof as these materials have especially high refractive index. Still even more preferably the whitening pigment is selected from titanium dioxide, zinc oxide or a mixture thereof and most preferred whitening pigment is titanium dioxide.

The average diameter of whitening pigment is typically from 15 nm to 2 microns, more preferably from 0.1 to 1 micron, even more preferably from 300 to 700 nm and most preferably from 380 nm to 580 nm.

Preferably the composition comprises whitening pigment in an amount of from 0.001 to 10%, more preferably 0.01 to 6%, even more preferably still 0.1 to 4%, still even more preferably from 0.2 to 3% and most preferably from 0.6 to 2.5% by weight of the composition.

To have a better product sensory, for example thickness, wetness, creaminess, and/or stickiness, the weight ratio of the whitening pigment to the benzotriazole derivative sunscreen is preferably greater than 6:1, more preferably from 7:1 to 100:1, even more preferably from 10:1 to 30:1.

Compositions of the present invention include a cosmetically acceptable carrier. The carrier is preferably a liquid. Water is the most common carrier. The composition is preferably an emulsion and more preferably and oil-in-water emulsion.

The composition may comprise water in amount of 35 to 95% by weight of the composition, more preferably from 45 to 92%, even more preferably from 50 to 90%, most preferably from 68% to 88% by weight of the composition.

A small amount of emulsifying surfactant may be present. Surfactants may be anionic, nonionic, cationic, amphoteric and mixtures thereof by preferably comprises a nonionic surfactant. The non-ionic surfactant is preferably selected from the group comprising fatty alcohol ethoxylates, fatty acid ethoxylates, alkyl phenol ethoxylates or polyoxyethylene sorbitan alkyl esters. Preferred non-ionic surfactants of the fatty alcohol ethoxylate class are sold under the brand names of Brij 35, Brij 97, Brij700, Brij 99, Brij 56, Brij 76, C12E07, and Brij S10. Preferred non-ionic surfactants of the fatty acid ethoxylate class are sold under the brand names of Myrj S20, Myrj S40, Myrj S40, Myrj S50, and PEG (polyethylene glycol)-100 stearate. Preferred non-ionic surfactants of the polyoxyethylene sorbitan alkyl esters class are sold under the brand names of Tween 21, Tween20, Tween40, Tween 60, Tween 65 tristearate, Tween 85 trioleate, and Tween 80. More preferably the surfactant is fatty acid ethoxylate, more preferably PEG-100 stearate. Levels may range, for example, from 0.1 to 5%, more preferably from 0.1 to 2%, optimally from 0.1 to 1% by weight. Advantageously the amount of surfactant present should not be sufficient for lather formation. In these instances, less than 2% by weight, preferably less than 1%, and optimally less than 0.5% by weight surfactant is present.

The composition may additionally comprise a variety of thickening agents Illustrative but not limiting are stearic acid, AcrylamideSodium Acryloyldimethyltaurate Copolymer (Aristoflex AVC), Hydroxyethyl AcrylateSodium Acryloyldimethyltaurate Copolymer, Polyacrylates (such as Carbomers including Carbopol® 980, Carbopol® 1342, Pemulen TR-2® and the Ultrez® thickeners). The particular preferred thickening agent is AcrylatesC10-30 Alkyl Acrylate Crosspolymer. Amounts of the thickeners may range, for example, from 0.05 to 10%, more preferably from 0.3 to 2% by weight of the composition.

The composition may additionally comprise silicones, polyhydric alcohols, fatty alcohols, hydrocarbons, triglycerides or a mixture thereof.

Silicones when present may range from 1% to 60%, more preferably from 5% to 40%, by weight of the composition. These silicones may be organic, silicone-containing or fluorine-containing, volatile or non-volatile, polar or non-polar.

Particularly preferred volatile silicone oils are cyclic volatile silicones wherein the repeating unit ranges from 3 to 5; and linear silicones wherein the repeating unit ranges from 1 to 7. Highly preferred examples of volatile silicone oils include cyclomethicones of varying viscosities, e.g., Dow Corning 200, Dow Corning 244, Dow Corning 245, Dow Corning 344 and Dow Corning 345 (commercially available from Dow Corning Corp.); SF-1204 and SF-1202 Silicone Fluids, GE 7207 and 7158 (commercially available from G.E. Silicones) and SWS-03314 (commercially available from SWS Silicones Corp.

Hydrocarbons may include mineral oil, petrolatum and polyalpha-olefins. Examples of preferred volatile hydrocarbons include polydecanes such as isododecane and isodecane (e.g. Permethyl-99A which is available from Presperse Inc.) and the C7-C8 through C12-C15 isoparaffins (such as the Isopar Series available from Exxon Chemicals).

Polyhydric alcohols may include propylyene glycol, dipropylene glycol, polypropylene glycol, polyethylene glycol, sorbitol, hydroxypropyl sorbitol, hexylene glycol, 1,3-butylene glycol, isoprene glycol, ethoxylated glycerol, propoxylated glycerol and mixtures thereof. Most preferred is glycerol known also as glycerin. The amount of polyhydric alcohol may range anywhere from 0.1 to 10%, preferably between 0.4 and 5% by weight of the composition.

Fatty alcohols may also be present. The term "fatty" refers to carbon chain lengths ranging from 10 to 30 carbon atoms. Illustrative of this category are lauryl alcohol, cetyl alcohol, stearyl alcohol, isostearyl alcohol and combinations thereof. Cetyl alcohol is more preferable.

Illustrative triglycerides but not limiting are sunflower seed oil, cotton oil, canola oil, soybean oil, castor oil, borage oil, olive oil, shea butter, jojoba oil and mixtures thereof. Mono- and di-glycerides may also be useful. Particularly preferable are glyceryl monostearate and glyceryl distearate.

The composition preferably additionally comprises one or more organic sunscreens. A wide variety of organic sunscreen is suitable for use in combination with the essential ingredients of this invention. Suitable UV-A/UV-B sunscreen include, 2-hydroxy-4-methoxybenzophenone, octyldimethyl p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, butylmethoxydibenzoylmethane, 2-hydroxy-4-methoxybenzophenone, octyldimethyl-p-aminobenzoic acid and mixtures thereof. The most suitable organic sunscreens are 2-ethylhexyl-p-methoxycinnamate, butylmethoxydibenzoylmethane or a mixture thereof.

A safe and effective amount of organic sunscreen may be used in the compositions useful in the subject invention. The composition preferably comprises from 0.1% to 10%, more preferably from 0.1% to 5%, of organic sunscreen excluding benzotriazole derivative sunscreen.

The composition of the invention may preferably further comprise a skin lightening agent. Vitamin B3 compounds (including derivatives of vitamin B3) e.g. niacin, nicotinic acid or niacinamide are the preferred skin lightening agent as per the invention, most preferred being niacinamide. Vitamin B3 compounds, when used, are preferably present in an amount in the range of 0.1 to 10%, more preferably 0.2 to 5% by weight of the composition.

The compositions of the present invention can comprise a wide range of other optional components. Examples include antioxidants, colorants, fragrance, and preservatives.

The skin care composition refers to a composition suitable for topical application to human skin, preferably is a leave-on product. The term "leave-on" as used with reference to compositions herein means a composition that is applied to or rubbed on the skin, and left thereon. The term "skin" as used herein includes the skin on the face (except eye lids and lips), neck, chest, abdomen, back, arms, under arms, hands, and legs. Preferably "skin" means includes the skin on the face (except eye lids and lips) and under arms, more preferably skin means skin on the face other than lips and eyelids.

The following examples are provided to facilitate an understanding of the invention. The examples are not intended to limit the scope of the claims.

EXAMPLES

Example 1

This example demonstrates the preparation of skin care compositions.

TABLE 1

| Ingredient | Sample (wt %, active level) | | | | | | | | |
| --- | --- | --- | --- | --- | --- | --- | --- | --- | --- |
| | 1 | 2 | 3 | 4 | 5 | 6 | 7 | 8 | 9 |
| Water | To 100 | To 100 | To 100 | To 100 | To 100 | To 100 | To 100 | To 100 | To 100 |
| Aluminum Starch Octenylsuccinate [a] | 0 | 0.84 | 2.52 | 0 | 0.84 | 0.84 | 0.84 | 0.84 | 0.84 |
| Methylene Bis-Benzotriazolyl Tetramethylbutylphenol [b] | 0.10 | 0.10 | 0.10 | 0 | 0 | 0.25 | 0.10 | 0.10 | 0.10 |
| Titanium dioxide [c] | 1.36 | 1.36 | 1.36 | 0 | 1.36 | 1.36 | 0 | 1.46 | 2.43 |
| Triethanolamine | 0.65 | 0.65 | 0.65 | 0.65 | 0.65 | 0.65 | 0.65 | 0.65 | 0.65 |
| Stearic Acid | 1.50 | 1.50 | 1.50 | 1.50 | 1.50 | 1.50 | 1.50 | 1.50 | 1.50 |
| Cetyl Alcohol | 0.60 | 0.60 | 0.60 | 0.60 | 0.60 | 0.60 | 0.60 | 0.60 | 0.60 |
| Isohexadecane | 1.00 | 1.00 | 1.00 | 1.00 | 1.00 | 1.00 | 1.00 | 1.00 | 1.00 |
| PEG-100 Stearate | 0.50 | 0.50 | 0.50 | 0.50 | 0.50 | 0.50 | 0.50 | 0.50 | 0.50 |
| Phenoxyethanol | 0.60 | 0.60 | 0.60 | 0.60 | 0.60 | 0.60 | 0.60 | 0.60 | 0.60 |
| Carbomer | 0.35 | 0.35 | 0.35 | 0.35 | 0.35 | 0.35 | 0.35 | 0.35 | 0.35 |
| Acrylates/C10-30 Alkyl Acrylate Crosspolymer | 0.10 | 0.10 | 0.10 | 0.10 | 0.10 | 0.10 | 0.10 | 0.10 | 0.10 |

[a] Dry flo pure, supplied by Akzo Nobel
[b] Tinosorb M supplied by BASF
[c] Oxyde de Titane Organophile W 877, titanium dioxide (CI 77891), supplied by Sensient A series of skin care compositions were formulated as shown in Table 1.

Example 2

This example demonstrates the effects of aluminum starch octenylsuccinate on creaminess perception.

The samples were evaluated by an trained sensory panel, comprised of sixteen members experienced in evaluating skin care products. The study was conducted in a room with controlled temperature, humidity and light. The panelists quantify various product attributes at various stages of the product experience, The product creaminess was in particular evaluated. Each sample was evaluated twice across the 16 panelists at random over the test period.

The protocol for the study was as follows: panelists used a standard cleanser to wash their face before product application and allowed their skin to equilibrate for 10 minutes. Then 1cc of each product was spread on hands and applied to the face. During or after the process, the panelists gave a mark (0-100) related to the application, kinesthetic, visual and tactile performance of each product.

Table 2 shows the average marks of product creaminess for samples 1-4. Higher mark means that the product has a better sensory on product creaminess. It was found that samples 1, 2, and 3 are significantly better ($p<0.05$) than sample 4; sample 2 is significantly better ($p<0.05$) than either samples 1 or sample 3. The creaminess perception was significantly improved by inclusion of aluminum starch octenylsuccinate in certain limits.

TABLE 2

| Samples | Aluminum Starch Octenyl-succinate | Methylene Bis-Benzotriazolyl Tetramethylbutyl-phenol | Titanium dioxide | product creaminess |
|---|---|---|---|---|
| 4 | 0 | 0 | 0 | 31.5 |
| 1 | 0 | 0.10 | 1.36 | 50.3 |
| 2 | 0.84 | 0.10 | 1.36 | 57.3 |
| 3 | 2.52 | 0.10 | 1.36 | 45.3 |

Example 3

This example demonstrates the effects of bis-benzotriazolyl tetramethylbutylphenol on creaminess perception.

The marks of product creaminess were obtained in the same way as described in Example 2. Table 3 shows the average marks of product creaminess for samples 2, 4, 5, and 6. Higher mark means that the product has a better sensory on product creaminess. It was found that samples 2, 5, and 6 are significantly better ($p<0.05$) than sample 4; sample 2 is significantly better ($p<0.05$) than either samples 5 or sample 6. The creaminess perception was significantly improved by incorporating methylene bis-benzotriazolyl tetramethylbutylphenol into the compositions in certain limits.

TABLE 3

| Samples | Aluminum Starch Octenyl-succinate | Methylene Bis-Benzotriazolyl Tetramethylbutyl-phenol | Titanium dioxide | product creaminess |
|---|---|---|---|---|
| 4 | 0 | 0 | 0 | 31.5 |
| 5 | 0.84 | 0 | 1.36 | 50.5 |
| 2 | 0.84 | 0.10 | 1.36 | 57.3 |
| 6 | 0.84 | 0.25 | 1.36 | 42.7 |

Example 4

This example demonstrates the effects of titanium dioxide on creaminess perception.

The marks of product creaminess were obtained in the same way as described in Example 2. Table 4 shows the average marks of product creaminess for samples 2, 4, 7-9. Higher mark means that the product has a better sensory on product creaminess. It was found that samples 2, 7-9 are significantly better ($p<0.05$) than sample 4, samples 2, 8, 9 are significantly better ($p<0.05$) than sample 7; sample 2 is on par with sample 8; and sample 2 is on par with sample 9. The presence of titanium oxide significantly improved the creaminess perception of the skin care compositions.

TABLE 4

| Samples | Aluminum Starch Octenyl-succinate | Methylene Bis-Benzotriazolyl Tetramethylbutyl-phenol | Titanium dioxide | product creaminess |
|---|---|---|---|---|
| 4 | 0 | 0 | 0 | 31.5 |
| 7 | 0.84 | 0.10 | 0 | 39.8 |
| 2 | 0.84 | 0.10 | 1.36 | 57.3 |
| 8 | 0.84 | 0.10 | 1.46 | 60.0 |
| 9 | 0.84 | 0.10 | 2.43 | 62.0 |

The invention claimed is:

1. A skin care composition comprising starch, benzotriazole derivative sunscreen, whitening pigment and a cosmetically acceptable carrier wherein the starch is present in amount of less than 2.2% by weight of the composition, and the benzotriazole derivative sunscreen is present in amount of less than 0.22% by weight of the composition, and further wherein the weight ratio of starch to benzotriazole derivative sunscreen is 5:1 to 10:1.

2. The composition according to claim 1 wherein the starch is aluminum starch octenylsuccinate.

3. The composition according to claim 1 wherein the starch is present in an amount of 0.001 to 2% by weight of the composition.

4. The composition according to claim 1 wherein the benzotriazole derivative sunscreen is methylene bis-benzotriazolyl tetramethylbutylphenol.

5. The composition according to claim 1 wherein the amount of the benzotriazole derivative sunscreen is 0.001 to 0.2% by weight of the composition.

6. The composition according to claim 1 wherein the starch is present in an amount from 0.6 to 1.2% by weight.

7. The composition according to claim 1 wherein the whitening pigment is titanium dioxide.

8. The composition according to claim 7 wherein the titanium dioxide has an average particle diameter from 0.1 to 1 micron.

9. The composition according to claim 7 wherein the titanium dioxide is present in an amount from 0.2 to 3% by weight of the composition.

10. The composition according to claim 1 wherein the composition further comprises non-ionic surfactant.

11. The composition according to claim 1 wherein the composition is an oil-in-water emulsion.

12. The composition according to claim 1 wherein the composition comprises from 50 to 90% of water by weight of the composition.

13. The composition according to claim 5 wherein the amount of benzotriazole derivative sunscreen is from 0.05 to 0.15% by weight of the composition.

14. The composition according to claim 6 wherein the benzotriazole derivative sunscreen is present in an amount from 0.07 to 0.12% by weight.

15. The composition according to claim 8 wherein titanium dioxide has an average particle size from 300 to 700 nm.

16. The composition according to claim 1 where the benzotriazole derivative sunscreen is methylene bis-benzotriazolyl tetramethylbutylphenol, the starch is aluminum starch octenylsuccinate wherein the starch is present at an amount from 0.6 to 1.2% by weight, the sunscreen is present 0.07 to 0.12% by weight and the whitening pigment is titanium dioxide having an average particle diameter from 300 to 700 nm.

* * * * *